United States Patent [19]

Copelin

[11] 4,175,009

[45] Nov. 20, 1979

[54] SEPARATION OF ALCOHOL FROM TETRAHYDROFURAN

[75] Inventor: Harry B. Copelin, Wilmington, Del.

[73] Assignee: E. I. Du Pont de Nemours and Company, Wilmington, Del.

[21] Appl. No.: 860,788

[22] Filed: Dec. 15, 1977

[51] Int. Cl.² .................. C07D 307/00; B01D 3/40
[52] U.S. Cl. ................................ 203/96; 203/92; 260/346.11
[58] Field of Search ............ 260/346.11, 643 R; 203/96, 95, 97, 92, 93, 83, 85, 76, 79; 568/913

[56] References Cited

U.S. PATENT DOCUMENTS

| | | | |
|---|---|---|---|
| 2,198,651 | 4/1940 | Bludworth | 260/346.11 |
| 2,551,626 | 5/1951 | Morrell et al. | 203/85 |

FOREIGN PATENT DOCUMENTS 51-146458  12/1976  Japan .

Primary Examiner—Wilbur L. Bascomb, Jr.

[57] ABSTRACT

A process for separating one or more aliphatic alcohols selected from the group consisting of methanol, ethanol, isopropanol and tertiary butanol from a tetrahydrofuran stream comprising tetrahydrofuran, one or more of said alcohols and optionally water by extractive distillation with water.

4 Claims, 4 Drawing Figures

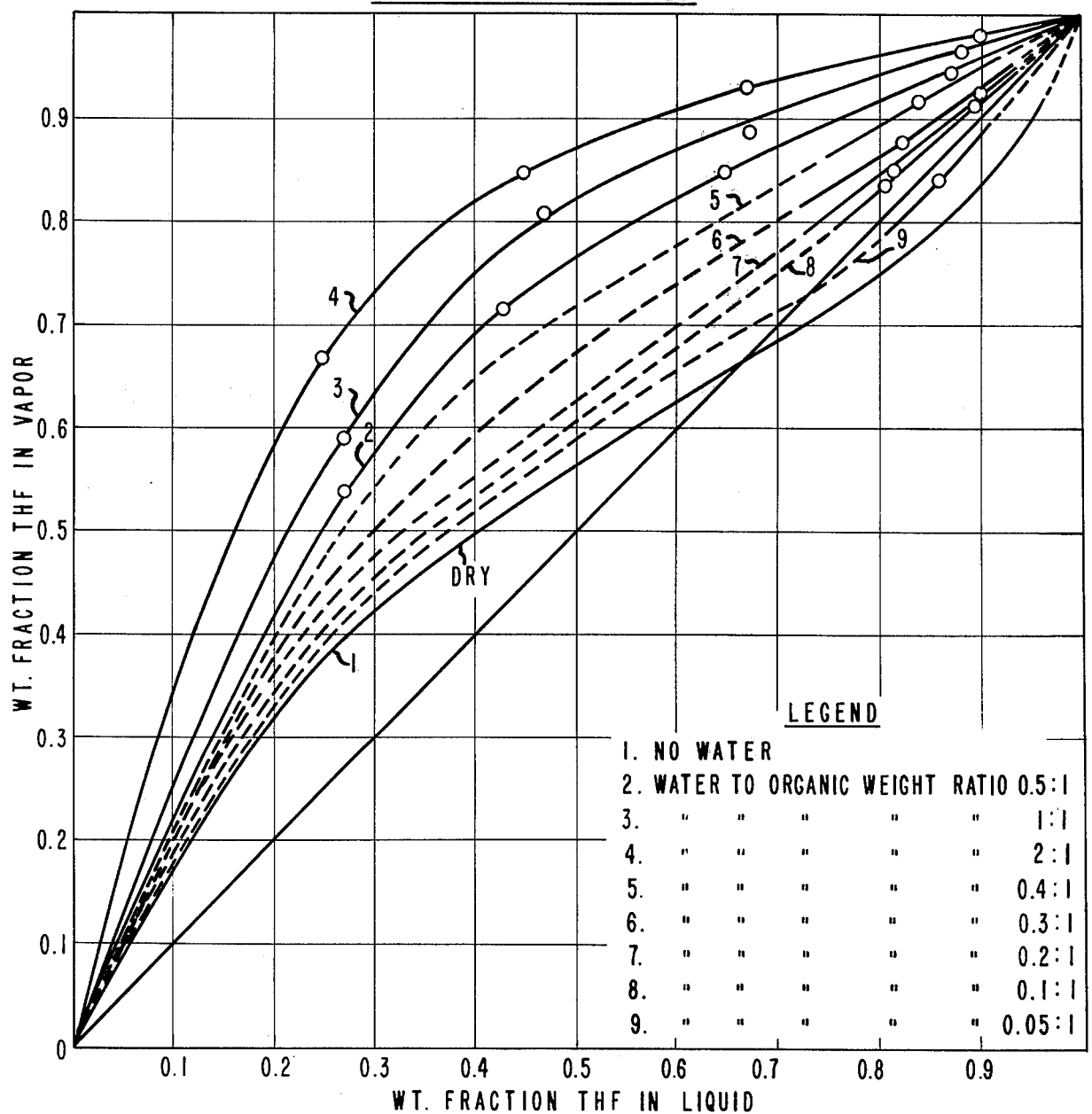

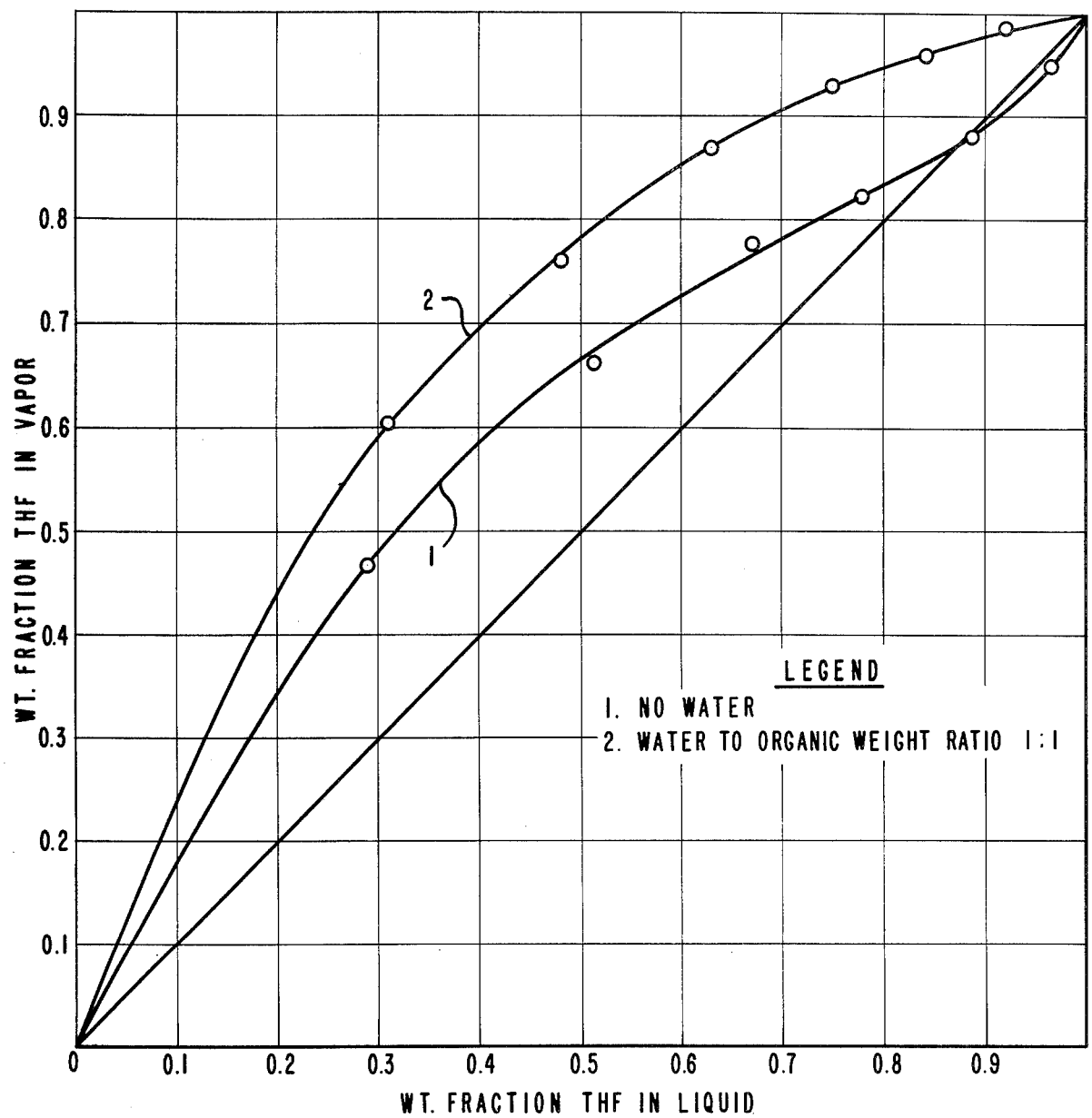

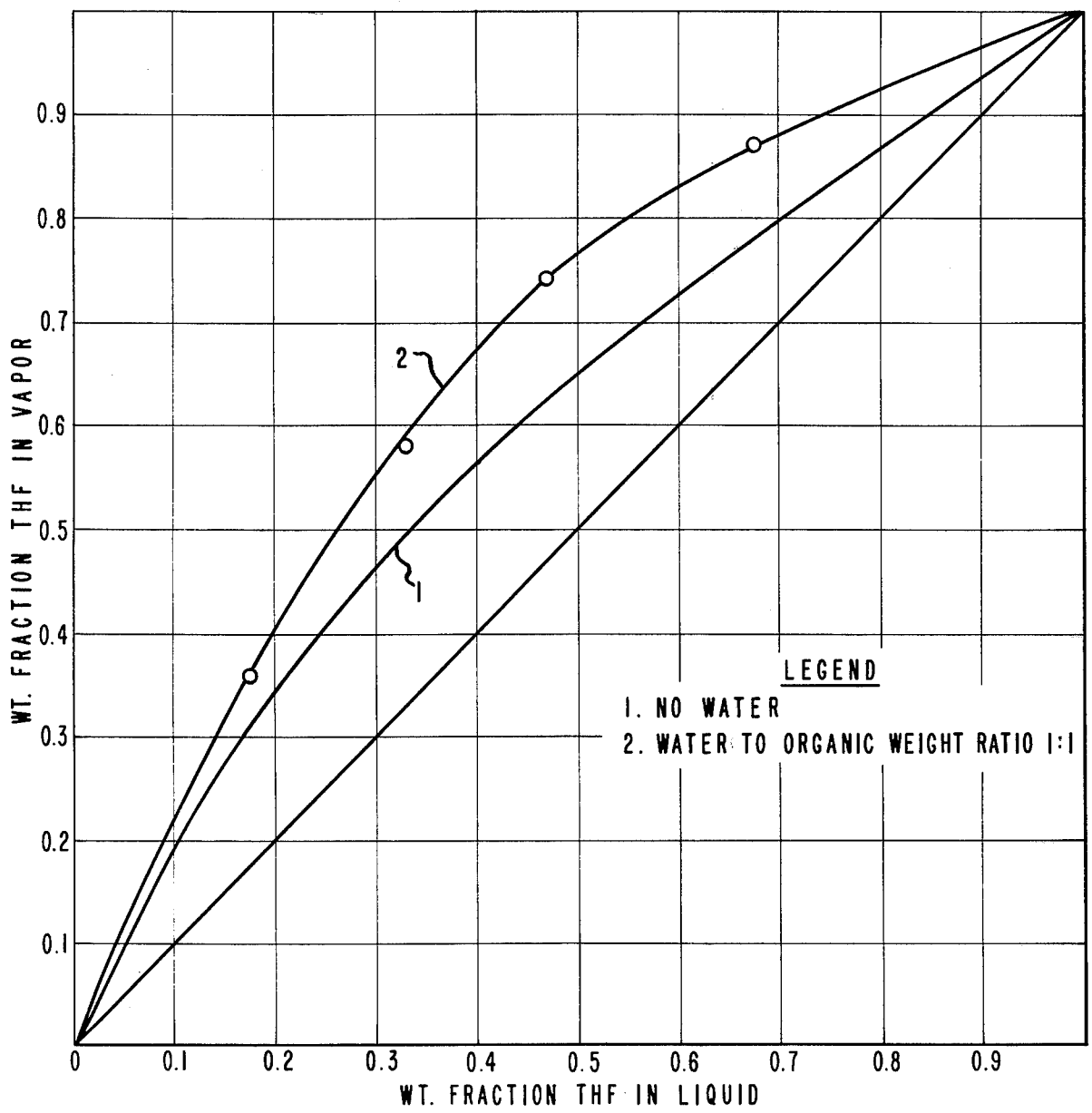

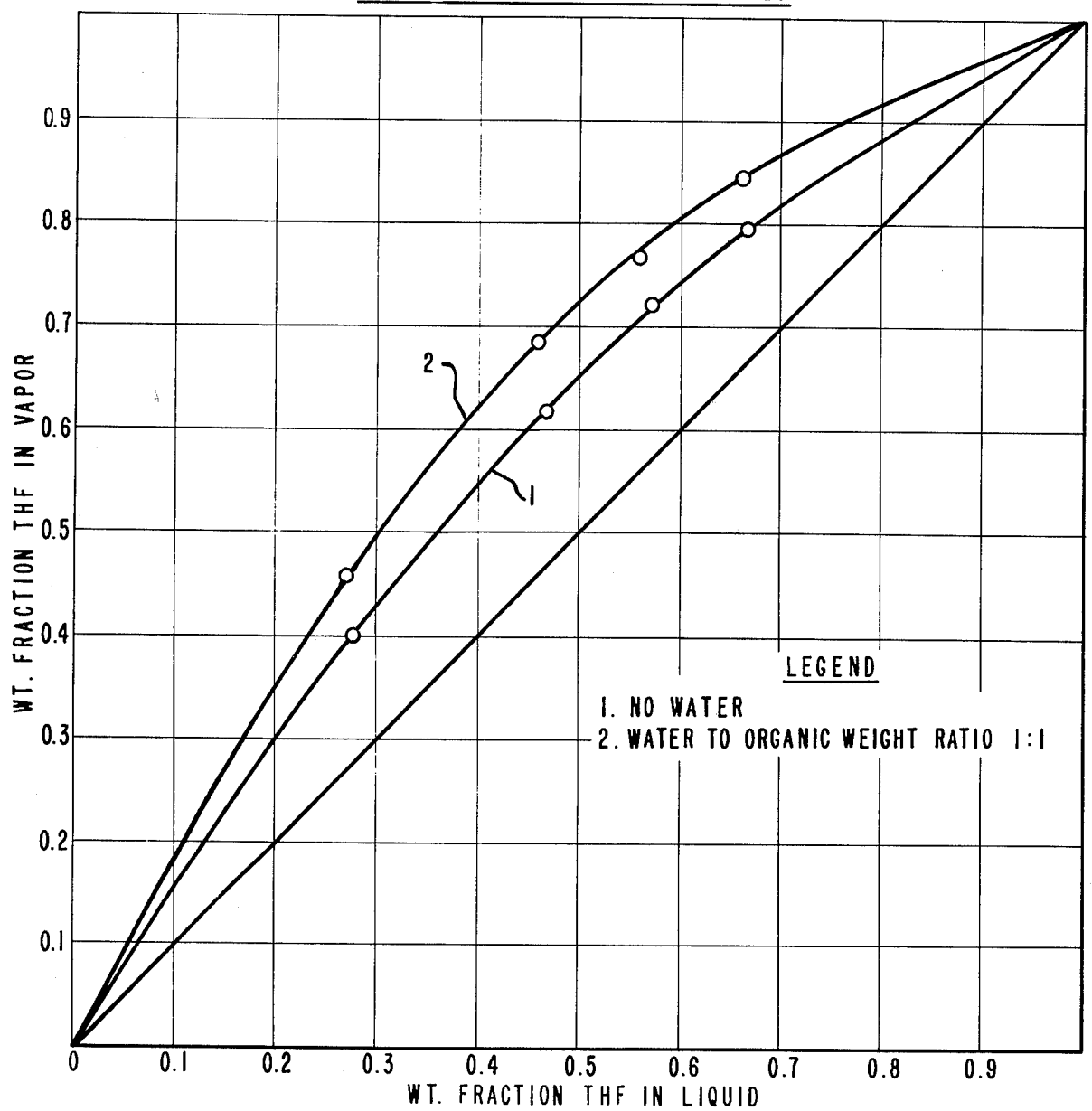

SEPARATION OF ALCOHOL FROM TETRAHYDROFURAN

BACKGROUND OF THE INVENTION

1. Field of Use

The process of this invention relates to a process for removing lower alcohols from a tetrahydrofuran stream. More particularly, the process of this invention relate to a process for removing lower alcohols from a tetrahydrofuran stream by extractive distillation with water.

2. Prior Art

In the production of tetrahydrofuran (THF) from acetylene and formaldehyde, crude 1,4-butanediol (BAD) is heated in a cyclization reactor in the presence of sulfuric acid to cyclize the BAD to form THF with water and small quantities of methanol. The THF and water produced are vaporized from the cyclization reactor through a distillation column with the small quantities of methanol. However, in the process of dehydrating the THF the amount of methanol tends to build up in the system due to the formation of a low boiling binary azeotrope between methanol and THF which is not readily separable by direct distillation. Methanol can be removed or reduced by means of a purge. Purging, to remove the methanol cannot be achieved without a loss of THF. It is estimated that for every pound of methanol removed from the system some 5 to 10 pounds of THF are lost.

BAD can also be produced by hydrogenation of a mixture of formyl acetals containing, for example, 2-$\beta$-formylethyl-5-methyl-1,3-dioxane. The product of said hydrogenation includes BAD, an aqueous byproduct mixture of lower alcohols and THF. This alcohol mixture may contain methanol, ethanol, normal propanol and normal and iso butanol. Recovery of a substantially pure THF-water azeotrope from this mixture is desirable. The separatin of n-propyl and the normal and isobutyl alcohols can be accomplished by direct distillation, but in the case of methanol and ethanol, due to azeotrope formation, separation cannot be made by direct distillation.

In the manufacture of polybutylene terephthalate resins by reaction of BAD with the methyl ester of the terephthalic acid, methanol and THF are formed. An efficient procedure is needed to separate THF and methanol.

U.S. Pat. No. 2,198,651 discloses a process for the separation of constant boiling ternary mixtures of an alcohol, acetone and an unsaturated compound(s) whereby two binary mixtures are formed. A ternary mixture disclosed is methanol, acetone and tetramethylene oxide (THF). In all mixtures disclosed, acetone is present. The scope of the disclosure and teaching is therefore limited to ternary mixtures containing acetone. Acetone is a known entrainer for THF in a wet system. In such a system, acetone would be taken overhead with the THF and thus be an undesirable contaminant.

SUMMARY OF THE INVENTION

Now it has been found that certain alcohols can be separated from tetrahydrofuran in a conventional distillation column by extractive distillation of the alcohol with water in the absence of acetone. The extractive distillation is achieved by contacting a tetrahydrofuran stream with water in a distillation column generally by adding water above the point where the tetrahydrofuran stream is fed to the column.

The alcohol which the present invention separates from the tetrahydrofuran is one or more of the group consisting of methanol, ethanol, isopropanol and tertiary butanol. The preferred alcohols subjected to the process of this invention are methanol and ethanol.

The tetrahydrofuran stream of this invention from which the alcohol is separated comprises tetrahydrofuran, one or more alcohols selected from the group consisting of methanol, ethanol, isopropanol and tertiary butanol and optionally water. Generally water is present in the tetrahydrofuran stream, but the process of this invention is operable without the presence of water in the THF stream.

Thus, the present invention involves a process for separating one or more alcohols selected from the group consisting of methanol, ethanol, isopropanol and tertiary butanol, from a mixture of tetrahydrofuran (THF), one or more of methanol, ethanol, isopropanol and tertiary butanol and optionally water, said process comprising feeding said mixture into a distillation column and extractively distilling THF from the mixture in said distillation column by adding water into the distillation column above the feed of said mixture to permit the countercurrent contact of the water and the mixture containing the alcohol to be separated. The alcohol(s) is removed from the bottom of the column as a water solution which can be further distilled to recover the alcohol. The THF is removed from the top of the column as a water azeotrope.

DESCRIPTION OF THE INVENTION

Mixtures of THF and one or more of said alcohols to be removed can result in a variety of ways. In reactions involving the cyclization of 1,4-butanediol to THF, one or more of the above alcohols form, thereby contaminating the tetrahydrofuran product of the reaction. The particular alcohol(s) that may be present with THF vary depending on the process for the preparation of the tetrahydrofuran or vary with the particular THF mixture. Such alcohols are difficult to separate from tetrahydrofuran by conventional distillation.

In the production of tetrahydrofuran (THF) from acetylene and formaldehyde, 1,4-butanediol, which is first formed, is converted to THF in the presence of an acid, e.g., sulfuric acid by a cyclization reaction. Certain amounts of methanol are produced in the cyclization reaction.

In another process, in which butanediol is produced by hydrogenation of a mixture of formyl acetals containing, for example, 2-$\beta$-formylethyl-5-methyl-1,3-dioxane, an aqueous byproduct mixture of lower alcohols and THF is produced. This alcohol mixture may contain methanol, ethanol, normal propanol and normal and iso butanol.

There are processes for the manufacture of polybutylene terephthalate resins in which 1,4-butanediol is reacted with the methyl ester of the terephthalic acid. Methanol is formed in the product which is frequently contaminated by THF formed from the butanediol during the exchange reaction and an efficient procedure is needed to separate THF and methanol.

It is desired to recover substantially pure THF-water azeotrope from the tetrahydrofuran stream of this invention. The separation of methanol and ethanol by direct distillation is impossible due to azeotrope formation and difficult with isopropanol and tertiary butanol due to relatively small volatility difference in the isopropanol-THF system and tertiary butanol-THF system.

Generally a weight ratio of water to organic feed (tetrahydrofuran and alcohol) of at least 0.1:1 is used. When a weight ratio of 0.1:1 or more of water to organic feed is added to the THF stream, the THF becomes more volatile than the alcohol over the whole composition range of the THF stream permitting THF to be removed as a water azeotrope from the top of the column wherein the extractive distillation is taking place while the alcohol, whose volatility is suppressed by the water, migrates down the column. The preferred ratio of water to organic feed is from 0.4:1 to 4:1. Ratios less than 0.1:1 do not result in the removal of substantially all of the alcohol. Thus, the lower limit of 0.1:1 is critical. Below 0.1:1 the relative volatility, within the range of weight fractions possible, will be less advantageous or in the case of methanol or ethanol an azeotrope with the THF will form making it impossible to remove all the ethanol or methanol. There is no upper limit of water to organic feed ratio. As the amount of water used is increased relative to the organic feed, the relative volatility of the THF increases but difficulties can arise regarding the presence of excessive amounts of water in the bottoms.

In the process of the invention there is a small amount of THF that is washed into the bottoms from the extractive distillation.

The greater the water feed relative to the organic feed, the greater the amount of THF present in the bottoms. Unless recovered from the bottoms, this THF is lost. Recovery of THF from bottom mixtures containing greater amounts of water is difficult and expensive. Therefore, excessive water feed should be avoided. It is therefore desirable to maintain said ratio at from 0.4:1 to 4:1. At weight ratios below 0.4:1 of water to organic feed, e.g., 0.3:1, 0.2:1 and 0.1:1, separation of the alcohol from the tetrahydrofuran is achieved but is more costly due to the need for a substantially greater number of plates in the distillation column as compared to where the weight ratio is 0.4:1 or above.

FIG. 1 shows a THF-methanol vapor liquid equilibrium curve at various levels of water addition at atmospheric pressure.

FIG. 2 shows a THF-ethanol vapor liquid equilibrium curve with and without a specific ratio of water at atmospheric pressure.

FIG. 3 shows a THF-isopropanol vapor equilibrium curve with and without a specific ratio of water at atmospheric pressure.

FIG. 4 shows a THF-tertiary butanol vapor equilibrium curve with and without a specific ratio of water at atmospheric pressure.

Referring now to FIG. 1 it can be seen that direct distillation is not a feasible method of removing methanol. Assuming a perfect distillation, the highest concentration of methanol which can be removed overhead when a dry mixture is used is the azeotrope with about 33% by weight methanol; thus substantially all of the methanol cannot be removed. It can be seen that at water to organic feed ratios of as low as 0.1:1 all of the methanol can be removed. At any given weight fraction of THF in the liquid, the weight fraction in the vapor is more concentrated when said water ratio is 0.1 or greater. Thus, in the present process, there is sufficient water to render the THF more volatile while the methanol whose volatility is suppressed migrates down the column. At ratios of from 0.1:1 to 0.4:1 of water to organic feed, all of the methanol can be removed but the reflux ratio and the required plates would not be as advantageous as when said ratios are more than 0.4:1. At ratios of greater than 0.4:1, the relative volatilities are more advantageous than in the range of 0.1:1 to 4:1. Note that the curves at various water-organic feed ratios is dotted in part. The dotted part is an extension of the curve from the data obtained based on curves known. Note also that the curve at a ratio of 0.05:1 extends below the 45° line.

Referring now to FIG. 2, it can be seen that the highest concentration of ethanol which can be obtained overhead is the azeotrope of ethanol and THF containing about 12% ethanol. However, at a ratio of 1:1 of water to organic feed (THF and ethanol) all of the ethanol can be removed.

Referring now to FIG. 3, it can be seen that no azeotrope is formed between THF and isopropanol but the separation of the isopropanol is difficult due to the fact that the relative volatility curve lies close to the 45° line.

Referring now to FIG. 4, it can be seen that no azeotrope is formed between THF and tertiary butanol but the separation of the tertiary butanol is difficult due to the fact that the relative volatility curve lies close to the 45° line.

The process of this invention is a method of separating alcohols, that are present in the THF stream of this invention, from THF. The THF in such a stream is recovered as a water azeotrope which contains, at atmospheric pressure, some 6% water. Methods for obtaining dry THF from the azeotrope, such as distillation or by treatment with caustic soda are well known.

The relative volatility of a mixture of two compounds is a number that indicates the relative ease of separation of the two compounds. The relative volatility, α, can be calculated by the use of the equation:

Relative Volatility, $\alpha = (X_B Y_A / Y_B X_A)$ wherein $X_A$ is the concentration of the more volatile compound in the liquid, $Y_A$ is the concentration of the more volatile compound in the vapor, $X_B$ is the concentration of the less volatile compound in the liquid and $Y_B$ is the concentration of the less volatile compound in the vapor. To illustrate such a calculation, using the equilibrium curve for methanol, FIG. 1, wherein a 2:1 ratio of water to organic feed and at a 80% THF, 20% methanol mixture it can be seen that where $X_A$ is 0.80, $Y_A$ is about 0.96 and where $X_B$ is 0.2, $Y_B$ is about 0.04. Thus α is calculated below:

$\alpha = (0.20 \times 0.96)/(0.04 \times 0.80) = 6.0$

Similarly calculated values follow:

| Water/Organic | α |
|---|---|
| 2.0 | 6.0 |
| 1.0 | 4.1 |
| 0.5 | 2.9 |
| 0.4 | 2.2 |
| 0.3 | 1.7 |
| 0.2 | 1.4 |
| 0.1 | 1.25 |
| 0.05 | 0.9 |
| 0 | 0.75 |

Thus, when said ratio is at least 0.1:1, THF becomes more volatile over the whole composition range, permitting it to be removed as a water azeotrope from the top of the column. Optimum water rates also depend on reflux ratio since the higher the reflux, the greater the flow of THF-alcohol(s) down the column. At a fixed reflux ratio and constant feed of THF-alcohol(s) the water feed rate will be chosen to give the desired composition throughout the column.

At an α of less than about 2.2, separation becomes difficult and expensive. The above data illustrates the remarkable improvement obtained in ease of separation of methanol and THF by water extractive distillation.

A conventional distillation column may be used to conduct the extractive distillation of this invention. The column may be operated at superatmospheric pressure to ease condensation of the THF-water azeotrope and reduce column size, but atmospheric pressure can also be used, particularly if a low pressure steam is available for heating. Little advantage is seen otherwise in superatmospheric pressure operation. As anyone skilled in the art would know, the particular temperature used will depend on the pressure selected. Generally, the present process is operable at pressures of from 5 psia to 100 psia or even more. Preferably, the pressure is from atmospheric to 50 psia. Pressures below 5 psia are difficult to attain. Pressures above 100 psia are operable, but no particular advantage is gained by such greater pressures.

The THF from which the alcohols are removed is useful as a solvent for resins and polymers.

The following examples further illustrate the invention. In the examples all percentages are by weight unless otherwise indicated.

EXAMPLE 1

A distillation column was set up to demonstrate the separations attained by use of the water by the extractive distillation process of this invention with THF and the alcohols of this invention. The column consisted of three sections of 1" I.D. glass tubing filled with 0.16" stainless steel protruded packing above a pot. The two lower sections were 15" long and the upper section 8". A mixture of THF and alcohol(s) was fed in between the two lower sections, and the water, when used, was fed at the bottom of the upper section. The pot was a 1-liter flask fitted with a constant level overflow device and heated with a Glas-col mantle. Reflux was provided by a Corad variable reflux head set at 2.5/1 for the purposes of these tests.

To the distillation column were fed the materials indicated below at the rates shown and the heat to the column was adjusted to provide the split indicated between products removed from the top of the column and from the still pot overflow.

Water feed: 270 g/hr.
Ratio of H₂0:Organic feed 1.8:1.

|  | Feed | Overhead | Bottoms |
| --- | --- | --- | --- |
| Rate g/hr | 156 | 152.0 | 274.0 |
| % MeOH | 2 | 0.1 | 1.1 |
| % THF | 92 | 93.9 | 0.1 |
| % H₂O | 6 | 6.0 | 98.8 |

The methanol in the THF was reduced to 0.1% in the material passing overhead in the distillation column. The weight of the THF lost per pound of methanol purged from the bottom of the column was 0.1.

It can readily be seen that substantially all of the methanol was removed or that a purge will lose about 0.1 of a part of THF per part of methanol removed.

COMPARATIVE EXAMPLES A, B AND C

To illustrate results that occur without a water addition, a series of three tests were carried out as a control with the heat to the column being adjusted to provide a varying split between the products removed from the top of the column and from the still pot overflow as described in Example 1 except for the conditions indicated below:

COMPARATIVE EXAMPLE A—(No Water Feed)

|  | Feed | Overhead | Bottoms |
| --- | --- | --- | --- |
| Rate g/hr | 400 | 12.0 | 388.0 |
| % MeOH | 2 | 10.5 | 1.74 |
| % THF | 92 | 87.4 | 91.96 |
| % H₂O | 6 | 2.1 | 6.30 |

COMPARATIVE EXAMPLE B—(No Water Feed)

|  | Feed | Overhead | Bottoms |
| --- | --- | --- | --- |
| Rate g/hr | 400 | 25.0 | 375.0 |
| % MeOH | 2 | 9.9 | 1.45 |
| % THF | 92 | 88.34 | 92.15 |
| % H₂O | 6 | 1.76 | 6.40 |

COMPARATIVE EXAMPLE C—(No Water Feed)

|  | Feed | Overhead | Bottoms |
| --- | --- | --- | --- |
| Rate g/hr | 400 | 75.0 | 325.0 |
| % MeOH | 2 | 5.16 | 0.91 |
| % THF | 92 | 92.44 | 92.29 |
| % H₂O | 6 | 2.40 | 6.80 |

The THF lost in the overhead was about 8.5 lb/lb methanol purged in Comparative Example A and in no comparative example was the methanol in the bottoms reduced below 0.9% from 2.0 initial.

EXAMPLE 2

Example 1 was repeated except the organic feed was a mixture containing 57% THF and 43% tertiary butanol without any water and distillation carried out for 3 hours, at which time a steady state had been achieved. The water feed was introduced at a rate of 920 g/hr. (Ratio of water to organic feed of 3.5:1.) Feed and product rates and compositions are shown below:

|  | Feed | Overhead | Bottoms |
| --- | --- | --- | --- |
| Rate g/hr | 265 | 160.0 | 1025.0 |
| % 3° BuOH | 43.4 | 1.0 | 11.1 |
| % THF | 56.6 | 93.0 | 0.1 |
| % H₂O | — | 6.0 | 88.8 |

COMPARATIVE EXAMPLE D—(No Water Feed)

A control experiment for comparison purposes was performed as per Example 2 except that no water was fed and the organic feed and rates were as indicated below:

| | Feed | Overhead | Bottoms |
|---|---|---|---|
| Rate g/hr | 400 | 220.0 | 180.0 |
| % 3° BuOH | 43 | 5.0 | 90.0 |
| % THF | 57 | 95.0 | 10.0 |

Thus, the amount of THF lost in a purge to remove the alcohol would be greater than when operating under the present invention.

EXAMPLE 3

Example 1 was repeated except that the organic feed did not contain water and the amount of water fed was 200 g/hr. The organic feed makeup and the conditions were as indicated below:

Water:organic feed ratio=0.5:1.

| | Feed | Overhead | Bottoms |
|---|---|---|---|
| Rate g/hr | 400 | 149.0 | 451.0 |
| % Isobutanol | 13.75 | <0.1 | 12.2 |
| % n-Propanol | 40.08 | <0.1 | 36.2 |
| % Ethanol | 9.25 | <0.1 | 8.2 |
| % Methanol | 0.35 | <0.1 | 0.3 |
| % THF | 36.57 | 94.0 | 0.9 |
| % $H_2O$ | — | 6.0 | 42.2 |

Substantially pure THF was recovered except for about 6% water.

COMPARATIVE EXAMPLE E—(No Water Feed)

A control experiment for comparison purposes was performed as per Example 3 except that no water was fed and the organic feed and rates were as indicated below:

| | Feed | Overhead | Bottoms |
|---|---|---|---|
| Rate g/hr | 400 | 164.0 | 236.0 |
| % Isobutanol | 13.75 | <0.1 | 23.6 |
| % n-Propanol | 40.08 | <0.1 | 69.2 |
| % Ethanol | 9.25 | 11.9 | 8.0 |
| % Methanol | 0.35 | 0.85 | <0.1 |
| % THF | 36.57 | 87.25 | 0.2 |

While the invention has been described in considerable detail in the above specification, it is to be understood that such detail is solely for the purpose of illustration and that variations can be made by those skilled in the art without departing from the spirit and scope of the invention.

What is claimed is:

1. A process for separating from a tetrahydrofuran stream comprising one or more aliphatic alcohols selected from the group consisting of methanol, ethanol, isopropanol and tertiary butanol, tetrahydrofuran, optionally water and in the absence of acetone wherein tetrahydrofuran is the major constituent, one or more of said alcohols, said process comprising feeding said tetrahydrofuran stream into a distillation column, extractively distilling said tetrahydrofuran stream in said distillation column by adding water into the distillation column above the feed of said tetrahydrofuran stream at a weight ratio of water to alcohol-tetrahydrofuran of from 0.4:1 to 4:1 and recovering tetrahydrofuran from the top of the column with substantially no alcohol.

2. The process of claim 1 wherein the alcohol is methanol.

3. The process of claim 1 wherein the alcohol is ethanol.

4. The process of claim 1 wherein the alcohol is methanol and ethanol.

* * * * *